(12) United States Patent
Duffy

(10) Patent No.: US 10,492,907 B2
(45) Date of Patent: Dec. 3, 2019

(54) VALVE DELIVERY SYSTEM

(71) Applicant: Medtronic Vascular, Inc., Santa Rosa, CA (US)

(72) Inventor: Niall Duffy, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 301 days.

(21) Appl. No.: 15/345,113

(22) Filed: Nov. 7, 2016

(65) Prior Publication Data

US 2018/0125654 A1    May 10, 2018

(51) Int. Cl.
*A61F 2/24* (2006.01)

(52) U.S. Cl.
CPC .......... *A61F 2/2436* (2013.01); *A61F 2/2418* (2013.01); *A61F 2/2427* (2013.01); *A61F 2/2433* (2013.01); *A61F 2/2469* (2013.01); *A61F 2230/0069* (2013.01); *A61F 2250/006* (2013.01)

(58) Field of Classification Search
CPC .............. A61F 2250/006; A61F 2/2418; A61F 2/2427; A61F 2/2433; A61F 2/2436; A61F 2220/0016; A61F 2220/005; A61F 2220/0075; A61F 2230/0054; A61F 2230/0069; A61F 2230/0076; A61F 2/243; A61F 2/2439; A61F 2/2469
USPC .............................................. 623/1.11, 2.11
See application file for complete search history.

(56) References Cited

U.S. PATENT DOCUMENTS

| | | | |
|---|---|---|---|
| 6,908,481 B2 | 6/2005 | Cribier | |
| 7,947,072 B2 | 5/2011 | Yang et al. | |
| 8,092,518 B2 | 1/2012 | Schreck | |
| 2006/0271173 A1* | 11/2006 | Delgado, III | A61F 2/2427 623/2.11 |
| 2009/0105794 A1 | 4/2009 | Ziarno et al. | |
| 2011/0054487 A1 | 3/2011 | Farnan | |
| 2012/0022633 A1 | 1/2012 | Olson et al. | |
| 2014/0088694 A1 | 3/2014 | Rowe et al. | |
| 2016/0113765 A1 | 4/2016 | Ganesan et al. | |
| 2016/0242901 A1 | 8/2016 | Keren | |

OTHER PUBLICATIONS

International Search Report and Written Opinion of the International Searching Authority for PCT/US2017/057587, dated Feb. 6, 2018, 16 pages.

* cited by examiner

*Primary Examiner* — Katherine M Shi

(74) *Attorney, Agent, or Firm* — Dicke, Billig & Czaja, PLLC

(57) ABSTRACT

A valve delivery system including a valve prosthesis, a first catheter, and a second catheter. The valve prosthesis comprises a first frame and a second frame. The first frame is configured to attach to the second frame. The first frame is releasably disposable at the distal end of the first catheter. The second catheter is slidably disposable over the first catheter. The second frame is releasably disposable at a distal end of the second catheter.

20 Claims, 6 Drawing Sheets

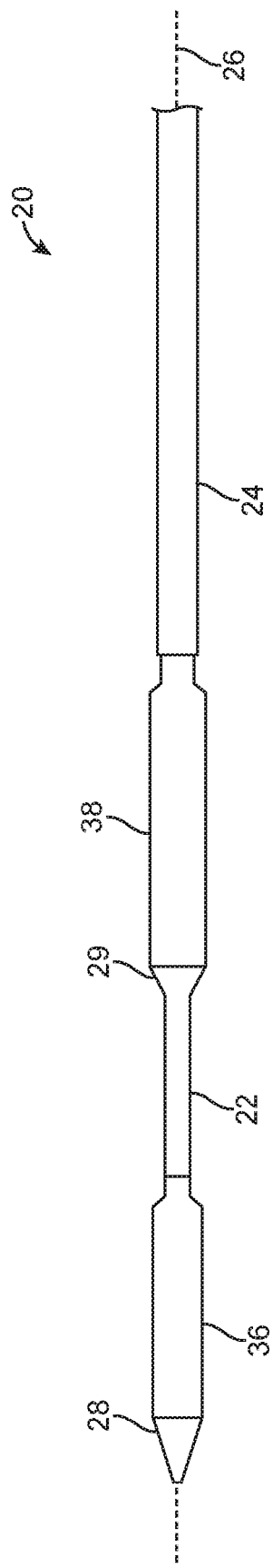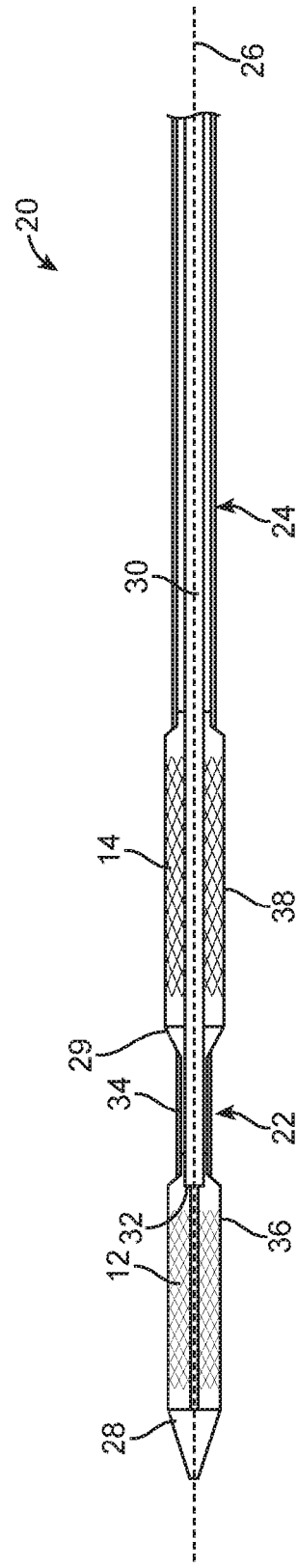

VALVE DELIVERY SYSTEM

BACKGROUND

The present disclosure relates to systems and methods for percutaneous implantation of a heart valve prosthesis. More particularly, it relates to systems and methods for transcatheter implantation of a prosthetic heart valve.

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus).

Various types and configurations of prosthetic heart valves are available for percutaneous valve procedures, and continue to be refined. The actual shape and configuration of any particular prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation systems, the stent frame of the valved stent is made of a self-expanding material and construction. With these systems, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation systems, the valved stent can be initially provided in an expanded or uncrimped condition, then crimped or compressed on a balloon portion of catheter until it is as close to the diameter of the catheter as possible. Once delivered to the implantation site, the balloon is inflated to deploy the prosthesis. With either of these types of percutaneous stent delivery systems, conventional sewing of the prosthetic heart valve to the patient's native tissue is typically not necessary.

The prosthetic valve can be large, presenting challenges in delivery into the anatomy for implantation. Delivery through the septum can present additional challenges. Two part prosthetic valves, wherein a first part of the valve is fastened to the second part of the valve can be less bulky to deliver, but delivery can be time consuming. Typically the first part is loaded and delivered on a catheter, then the catheter must be withdrawn, and then the second part is delivered and fastened to the first part.

In light of the above, a need exists for a more efficient manner of delivering and deploying a two part prosthetic valve.

SUMMARY

One aspect of the present invention relates to a valve delivery system including a valve prosthesis, a first catheter, and a second catheter. The valve prosthesis comprises a first frame and a second frame. The first frame is configured to attach to the second frame. The first frame is releasably disposable at the distal end of the first catheter. The second catheter is slidably disposable over the first catheter. The second frame is releasably disposable at a distal end of the second catheter.

Another aspect of the present invention relates to a method of implanting a valve prosthesis. The method includes advancing a first frame disposed at a distal end of a first catheter distal into a patient's vasculature, positioning the first frame distal to a native valve, advancing a second frame disposed at a distal end of a second catheter into a patient's vasculature, the second catheter disposed around the first catheter, positioning the second frame at a native valve annulus of the native valve, expanding the second frame at the valve annulus, repositioning the first frame at the valve annulus, expanding the first frame, and securing a first frame to the second frame. At least a portion of the first frame is within at least a portion of the second frame when the first frame is expanded.

Another aspect of the present invention relates to a method of implanting a valve prosthesis. The method includes advancing a first frame disposed at a distal end of a first catheter distal into a patient's vasculature and advancing a second frame disposed at a distal end of a second catheter into a patient's vasculature. The second catheter and second frame is disposed around the first catheter. The method also includes positioning the first frame at a native valve, deploying the first frame, repositioning the second frame at the native valve, deploying the second frame, receiving the second frame within the first frame, and securing the second frame to the first frame.

BRIEF DESCRIPTION OF THE DRAWINGS

FIG. 2A is a schematic side view illustration of an example delivery system in accordance with aspects of the present disclosure;

FIG. 2B is a schematic cross-sectional view illustration of an example delivery system in accordance with aspects of the present disclosure;

DETAILED DESCRIPTION

A prosthetic heart valve as used in accordance with the various systems, devices, and methods of the present disclosure may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the prosthetic heart valve useful with the systems, devices, and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

Figure 1A:
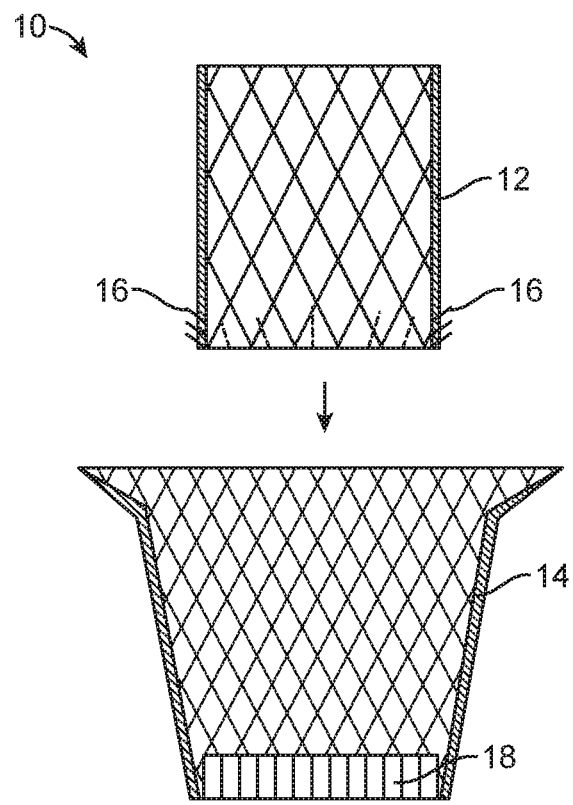
FIGS. 1A-1B are schematic cross-sectional illustrations of an example two-part prosthetic heart valve deliverable in accordance with aspects of the present disclosure.
Figure 1B:
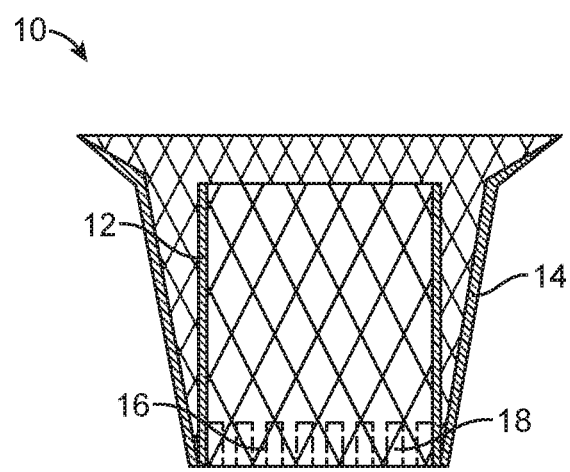

FIGS. 1A-1B are schematic cross-sectional illustrations of an example two-part prosthetic heart valve 10 deliverable in accordance with aspects of the present disclosure. In general terms, the prosthetic heart valve 10 deliverable in accordance with the delivery system 20 (see, e.g., FIGS. 2A-2B) of the present disclosure include a first frame 12 and a second frame 14 coupleable to the first frame 12, with the first and second frames 12, 14 having normal, expanded arrangements and collapsible to compressed arrangements for independent loading onto the delivery system. FIG. 1A illustrates the first frame 12 and the second frame 14 of an example prosthetic heart valve 10 in an unassembled expanded arrangement and FIG. 1B illustrates the first frame 12 and second frame 14 in an assembled expanded arrangement. The first and second frames 12, 14 can be coupled together after delivery and expandable deployment at the desired position within the patient, as discussed further below.

The prosthetic valve 10 can be any valve suitable to be delivered and deployed within the patient as two separate portions, or frames 12, 14, and is sized and shaped as appropriate for the type of heart valve replacement needed. The frames 12, 14 are support structures that can comprise a number of struts or wire portions arranged relative to each other to provide a desired compressibility and strength to the prosthetic heart valve 10. In one example embodiment, the second frame 14 can be a valvular structure frame and the first frame 12 can be a reinforced frame. In one embodiment, the frames 12, 14 are generally tubular support structures, with the second frame 14 including valve structure leaflets. The leaflets can be formed from a variety of materials, such as autologous tissue, xenograph material, or synthetics as are known in the art. In one embodiment, the frames can be formed using high-strength nano-manufactured NiTi films produced at Advance BioProsthetic Surfaces (ABPS), for example. The second frame 14 generally includes at least two (or three) leaflets; however, replacement prosthetic heart valves of the types described herein can incorporate more or less than three leaflets.

The second frame 14 that is fastened to the first frame 12 can be less bulky than the first frame 12. In one example illustrated in FIGS. 1A-1B, the first frame 12 can have a substantially truncated hyperboloidal shape in an expanded position, with a larger base and smaller neck. The first frame 12 can have a curvature that is concave towards the aortic wall. The second frame 14 can be a substantially cylindrical structure. The first frame 12 is expandable and capable of maintaining the body channel open in its expanded state and supporting the collapsible second frame 14. In one embodiment, the first and second frames 12, 14 each have mateable couplers 16, 18 that securely fasten the first and second frames 12, 14 together. Any suitable coupling means are acceptable. A perimeter of the second frame 14 is coupled to an interior portion of the first frame 12. The first frame 12 is fastened along a substantial portion of the second frame 14. In one embodiment, the frames 12, 14 are self-expanding and are formed of a shaped memory alloy, for example. In another embodiment, the first and second frames 12, 14 are balloon expandable.

FIGS. 2A and 2B are schematic side and cross-sectional view illustrations of an example valve delivery system 20 in accordance with aspects of the present disclosure. The valve delivery system 20 includes a first catheter 22 and a second catheter 24 coaxially disposed over the first catheter 22. The first and second catheters 22, 24 are slidably disposed relative to one another along a longitudinal axis 26. The two part valve delivery provides that each frame 12, 14 of the two part prosthetic heart valve 10 has a smaller external diameter when in collapsed states, since each frame 12, 14 to be expanded, considered separately, is smaller than in combination. The valve delivery system 20 distally stores and delivers the two portions, or frames 12, 14, of the prosthetic heart valve 10. For example, during delivery a distal end 28 of the first catheter 22 can be proximal to, but spaced from, a distal end 29 of the second catheter 24.

The first frame 12 can be collapsed and loaded onto a first, inner, catheter 22 and the second frame 14 can be collapsed and loaded onto the second catheter 24 in preparation of delivery. The second catheter 24 and the second frame 14 are circumferentially and coaxially disposed around the first catheter 22. With additional reference to FIGS. 3A-3D, a guide wire can be disposed within a lumen 30 of the first catheter 22 to help position the first and second frames 12, 14 of the implantable valve 10 within the native valve opening. Additionally, in some embodiments, at least the first catheter 22 can include an inner tube 32 and an outer tube 34 with the inner tube 32 to prevent the stent-graft from moving back as a capsule sheath 36 is withdrawn. In one embodiment, capsules 36, 38 are disposed at the distal ends 28, 29 of the first and second catheters 22, 24, respectively, to releasably contain the first and second frames 12, 14 for delivery. In another embodiment, instead of capsule sheaths, at least one of the distal ends 28, 29 of the first and second catheters 22, 24 include inflatable balloons that the first and second frames 12, 14 are disposed.

FIGS. 3A-3D are schematic illustrations of a method of delivering a two-part prosthetic heart valve 100 with a valve delivery system 200 of the present disclosure. Intraluminal deployment is effected using the valve delivery system 200, similar to that of valve delivery system 20 described above. As described below, a first frame 112 and a second frame 114 are independently and coaxially collapsed for delivery and independently and coaxially expanded when deployed. A first catheter 222 and a second catheter 224 are arranged for relative axial movement with the first and second frames 112, 114 compressed and disposed onto the distal ends of the first and second catheters 222, 224, respectfully.

Figure 3A:
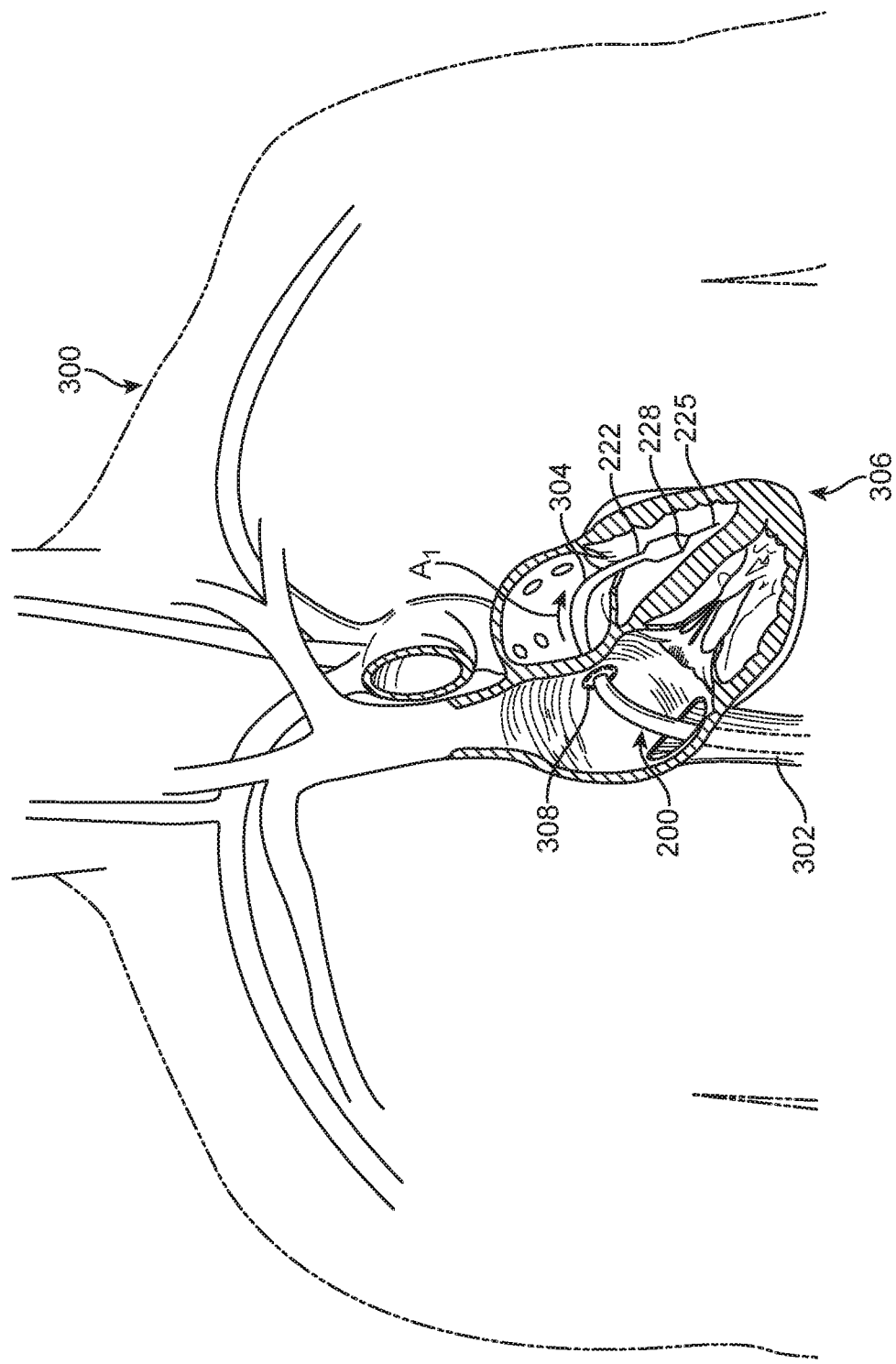
FIGS. 3A-3D are schematic illustrations of a method of delivering a two-part prosthetic heart valve in accordance with aspects of the present disclosure.

In one embodiment, as illustrated in FIG. 3A, the first catheter 222 is maneuvered, typically routed through a vessel 302 (e.g., lumen) of a patient 300, until a distal end 228 of the first catheter 222 upon which the first frame 112 is releasably disposed, is positioned in the vicinity of the intended treatment site, such as a native valve 304 of a heart 306. The first, inner, catheter 222 is tracked in over a guide wire 225 in a direction indicated by arrow $A_1$ to position a distal end 228 (including, e.g., a first capsule or a first balloon) of the first catheter 222 for disposing the first frame 112 in a position that extends the first catheter 222 through and past the native valve 304. As illustrated, the delivery path can occur through the patient's septum 308 and continue by turning approximately 90° downward through the native mitral valve 304.

Figure 3B:
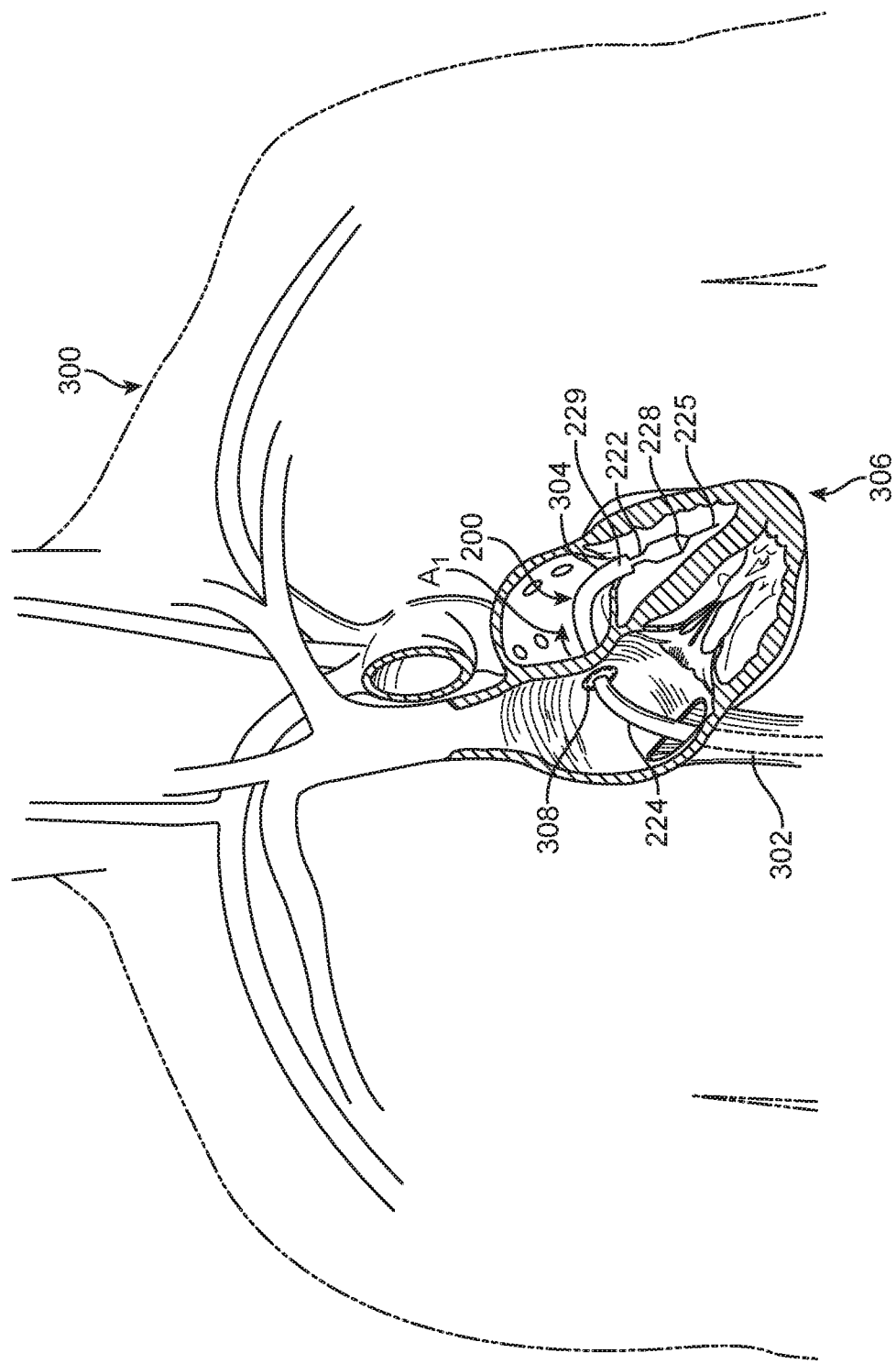

As illustrated in FIG. 3B, the second catheter 224 is then tracked over the guide wire 225 and over the first catheter 222 in the direction indicated by arrow $A_1$ to position a distal end 229 (including, e.g., a second capsule or a second balloon) upon which the second frame 114 is releasably disposed, within the native valve 304 opening and into the desired deployment position. The first catheter 222 can assist with centering of the second catheter 224 and second frame 114 both coaxially disposed around the first catheter 222 within the native valve 304 opening. As the first catheter 222 carrying the first frame 112 at the distal end 228 remains extended through the native valve 304, the native valve 304 function is inhibited. The second catheter 224 carrying the second frame 114 at the distal end 229 can be quickly moved into position with coaxially routed over the first catheter 222 to deploy the first and second frames 112, 114 and begin valve function can begin again, as described further below.

The first and second catheter 222, 224 of the valve delivery system 200 are successively, coaxially disposed with respect to the native valve 304. During insertion and routing along the delivery pathway, the distal end 229 of the second catheter 224 is spaced from the distal end 228 of the first catheter 222 such that a portion of the first catheter 222 is exposed between the two distal ends 228, 229. In one embodiment, the portion of the first catheter 222 between the distal ends 228, 229 is relatively small such that the first distal end 228 can be quickly delivered and repositioned to deploy the first frame 112 after the second frame 114 is deployed. The portion of the first catheter 222 extending between the first and second distal ends 228, 229 can perform a hinge-like function to facilitate navigation of bends in the delivery path. In this manner, the catheters 222, 224 can bend and the first and second frames 112, 114 releasably contained or disposed therein can traverse a more tortuous delivery path than otherwise possible with a single, larger delivery payload of a complete prosthetic valve or if the two parts, or frames 112, 114, were disposed together longitudinally in a series.

Figure 3C:
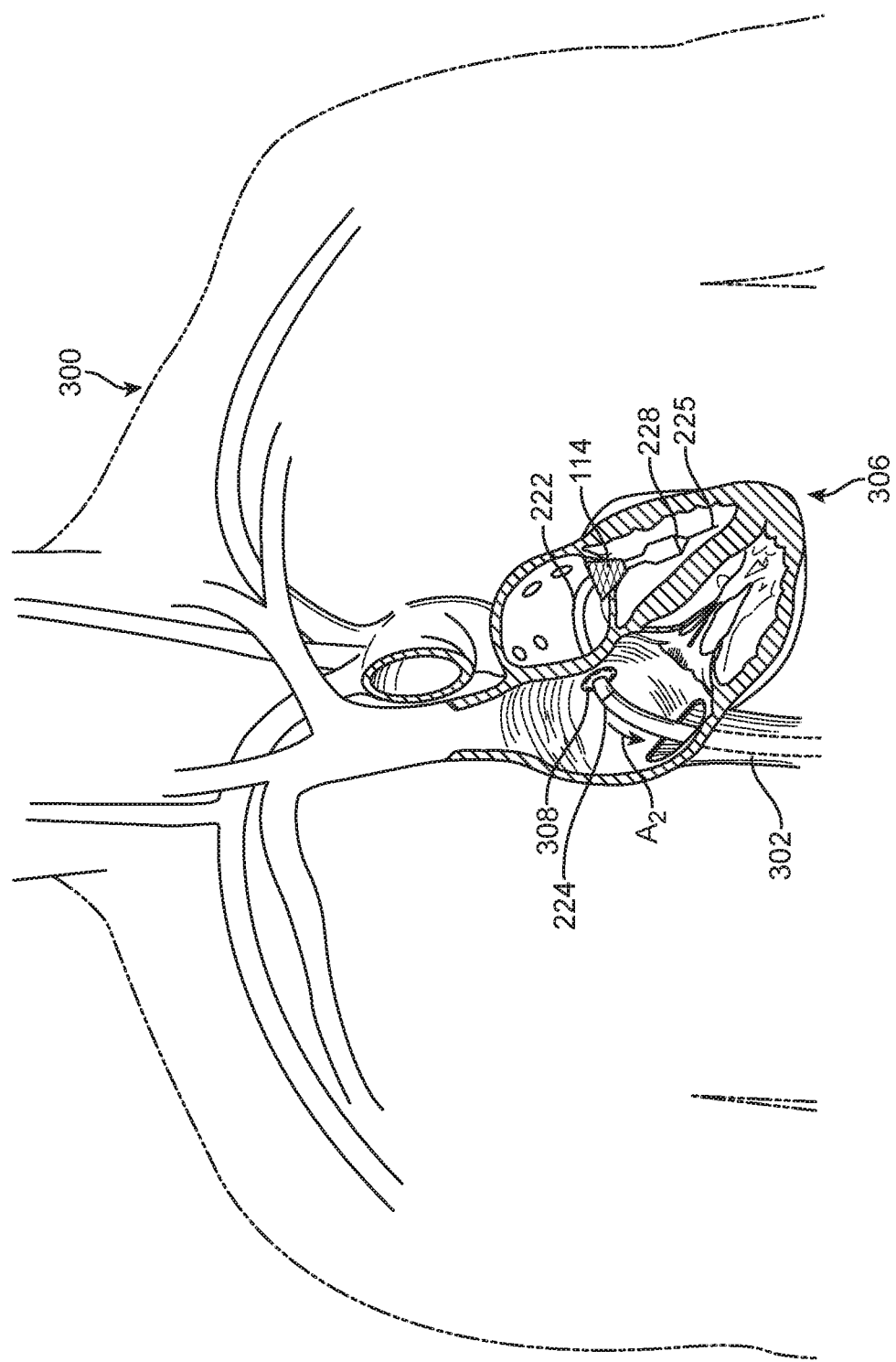

With reference to FIG. 3C, the first catheter 222 is maintained distal to the native valve 304 while the second catheter 224 is withdrawn along the first catheter 222 in a direction indicated by arrow $A_2$. As the second catheter 224 is withdrawn, the second frame 114 is gradually exposed. The exposed portion of the second frame 114 radially expands so that at least a portion of the expanded portion is in substantially conforming surface contact with a portion of the interior of the native heart valve 304 opening. The second frame 114 is fully deployed and released from the distal end 229 and the second catheter 224 is withdrawn.

Figure 3D:
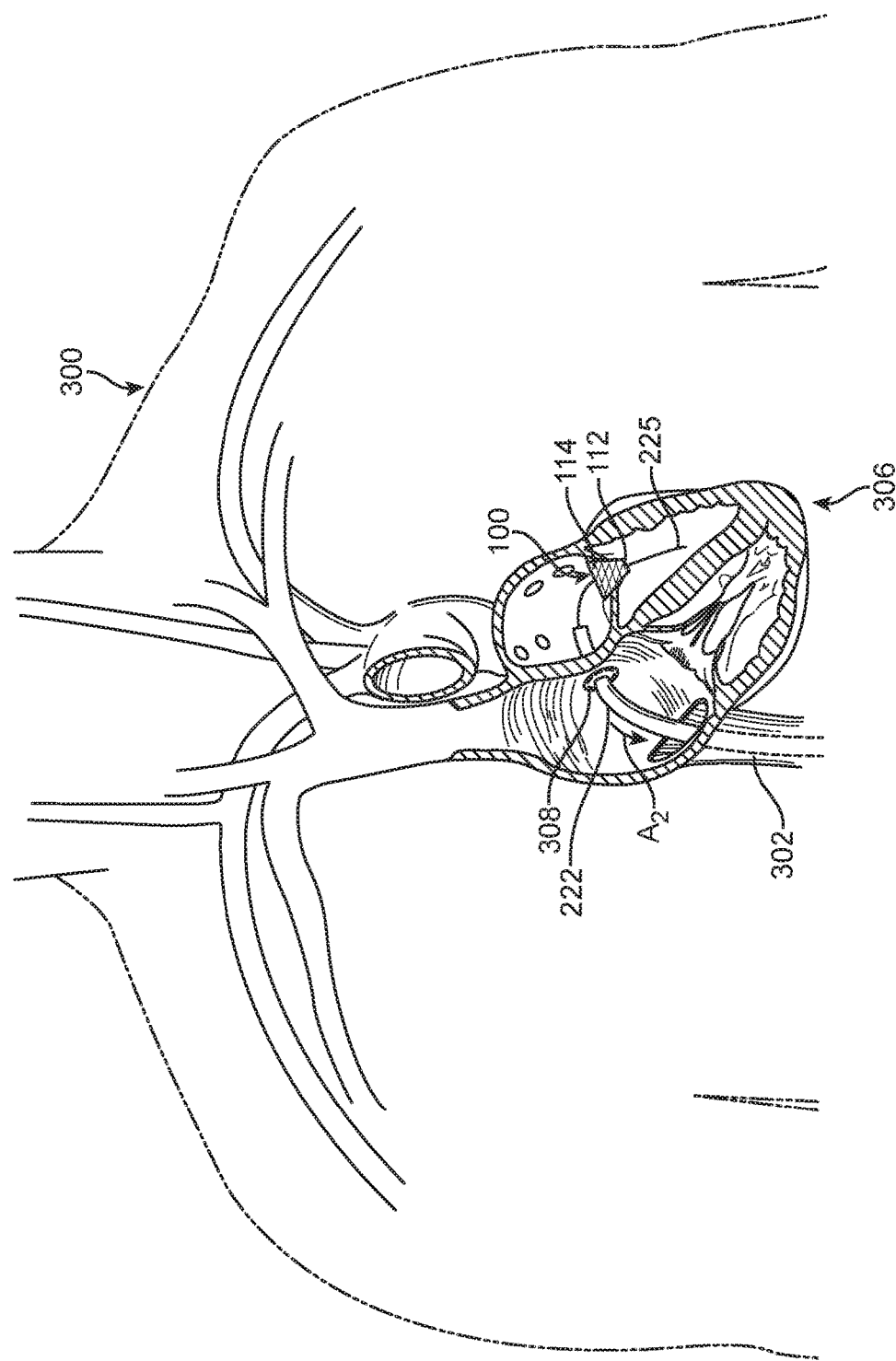

With reference to FIG. 3D, the first catheter 222 is withdrawn along the guide wire 225 in the direction indicated by arrow $A_2$ to reposition the first distal end 228 containing the first frame 112 at least partially within the second frame 114 and the native valve 304 opening. The first frame 112 is deployed and the first frame 112 expands within the second frame 114. The first and second frames 112, 114 are secured together. The attachment of the first and second frames 112, 114 can be via matable couplers as described above with respect to FIGS. 1A-1B, for example, or via any other suitable secure attachment. After the first frame 112 is fully deployed, the first catheter 222 can then continue to be withdrawn along the delivery path in the direction indicated by arrow $A_2$.

The first and second catheters 222, 224 may be inserted, routed and deployed in any order and are not limited to the order described above. Further, in one embodiment, both the first and second frames 112, 114 are self-expanding. In another embodiment, both the first and second frames 112, 114 are balloon expandable. In another embodiment, one of the first and second frames 112, 114 is self-expanding and the other of the first or second frame 112, 114 is balloon expandable.

Although the present disclosure has been described with reference to preferred embodiments, workers skilled in the art will recognize that changes can be made in form and detail without departing from the spirit and scope of the present disclosure.

What is claimed is:

1. A method of implanting a valve prosthesis, comprising:
    advancing a first frame disposed at a distal end of a first catheter distal into a patient's vasculature;
    positioning the first frame distal to a native valve;
    advancing a second frame disposed at a distal end of a second catheter into a patient's vasculature, the second catheter disposed around the first catheter;
    positioning the second frame within an opening of a native valve annulus of the native valve;
    expanding the second frame within the opening;
    repositioning the first frame within the opening;
    expanding the first frame, wherein at least a portion of the first frame is within at least a portion of the second frame; and
    securing a first frame to the second frame.

2. The method of claim 1, further comprising:
    centering the second frame within the native valve annulus with the first catheter.

3. The method of claim 1, wherein the first and second frames are independently deployed.

4. The method of claim 1, further comprising:
    withdrawing the first catheter independent of the second catheter.

5. The method of claim 1, wherein securing the first frame to the second frame includes mating self-mating couplers of the first and second frames.

6. The method of claim 1, wherein deploying the first frame includes releasing the first frame from a containment capsule and the first frame self-expanding.

7. The method of claim 1, wherein deploying the second frame includes releasing the second frame from a containment capsule and the second frame self-expanding.

8. The method of claim 1, wherein deploying the first frame includes inflating the first frame with a balloon.

9. The method of claim 1, wherein deploying the second frame includes inflating the second frame with a balloon.

10. The method of claim 1, wherein the first frame has a truncated hyperboloidal shape.

11. The method of claim 1, wherein the first frame has a curvature that is concave toward an aortic wall of the patient.

12. The method of claim 1, wherein the step of advancing a first frame disposed at a distal end of a first catheter distal into a patient's vasculature includes advancing the first frame through a septum of the patient.

13. A method of implanting a valve prosthesis within an opening of a native valve, the method comprising:
    advancing a first frame disposed at a distal end of a first catheter distal into a patient's vasculature;

advancing a second frame disposed at a distal end of a second catheter into a patient's vasculature, the second catheter and second frame disposed around the first catheter;
deploying the second frame within the opening of the native valve;
positioning the first frame within the opening of the native valve;
deploying the first frame;
receiving the first frame within the second frame; and
securing the second frame to the first frame.

14. The method of claim 13, wherein first and second frames are spaced apart from one another along a longitudinal axis defined by the first catheter when advanced through the patient's vasculature.

15. The method of claim 13, further comprising:
releasably constraining at least one of the first and second frames in a capsule prior to deploying.

16. The method of claim 15, wherein at least one of the first and second frames is self-expanding.

17. The method of claim 13, further comprising:
centering the second frame within the native valve with the first catheter.

18. The method of claim 13, wherein the first frame has a truncated hyperboloidal shape.

19. The method of claim 13, wherein the first frame has a curvature that is concave toward an aortic wall of the patient.

20. The method of claim 13, wherein the step of advancing a first frame disposed at a distal end of a first catheter distal into a patient's vasculature includes advancing the first frame through a septum of the patient.

* * * * *